United States Patent
Senee

(10) Patent No.: US 7,078,049 B2
(45) Date of Patent: Jul. 18, 2006

(54) ULTRAFINE EMULSION CONTAINING A HALOALKYNYL DERIVATIVE

(75) Inventor: Jerome Senee, Lardy (FR)

(73) Assignee: L'Oreal, Paris (FR)

( * ) Notice: Subject to any disclaimer, the term of this patent is extended or adjusted under 35 U.S.C. 154(b) by 4 days.

(21) Appl. No.: 10/254,678

(22) Filed: Sep. 26, 2002

(65) Prior Publication Data

US 2003/0073689 A1   Apr. 17, 2003

(30) Foreign Application Priority Data

Sep. 28, 2001  (FR) ................................. 01 12528
Feb. 5, 2002   (FR) ................................. 02 01341

(51) Int. Cl.
*A61K 6/00* (2006.01)
*A61K 9/70* (2006.01)
*A61K 8/00* (2006.01)
*B01F 3/08* (2006.01)

(52) U.S. Cl. .................. 424/401; 424/443; 424/63; 424/64; 424/70.1; 424/61; 516/53

(58) Field of Classification Search ................ 424/401, 424/443, 61, 63, 64, 70.1, 423, 426; 516/53
See application file for complete search history.

(56) References Cited

U.S. PATENT DOCUMENTS

| 3,450,812 A | * | 6/1969 | Harris .......................... 424/49 |
| 5,827,522 A | | 10/1998 | Nowak |
| 5,858,936 A | * | 1/1999 | Tamura et al. ............... 510/131 |
| 5,952,395 A | * | 9/1999 | Lorant ...................... 514/772.4 |
| 5,965,594 A | | 10/1999 | Schoenberg et al. |
| 5,968,528 A | | 10/1999 | Deckner et al. |
| 6,217,889 B1 | * | 4/2001 | Lorenzi et al. ............. 424/401 |

FOREIGN PATENT DOCUMENTS

| FR | EP 08194427 A1 | 1/1998 |
| WO | WO 93/14630 | 8/1993 |
| WO | WO 98/18441 | 5/1998 |
| WO | WO 98/47469 | 10/1998 |
| WO | WO 99/59709 | 11/1999 |
| WO | WO 01/03658 A1 | 1/2001 |

OTHER PUBLICATIONS

Wenninger et al. 'International Cosmetic Ingredient Dictionary and Handbook,' 1997, pp. 450.*

* cited by examiner

*Primary Examiner*—Shengjun Wang
(74) *Attorney, Agent, or Firm*—Oblon, Spivak, McClelland, Maier & Neustadt, P.C.

(57) ABSTRACT

A composition in the form of an ultrafine oil-in-water emulsion in which the mean size of the oil globules ranges from 50 nm to 1000 nm containing a haloalkynyl derivative, preferably 3-iodo-2-propynyl butylcarbamate.

49 Claims, No Drawings

ULTRAFINE EMULSION CONTAINING A HALOALKYNYL DERIVATIVE

This application claims foreign priority of France application 01 12528 filed on Sep. 28, 2001, and France application 02 01341 filed Feb. 5, 2002.

FIELD OF THE INVENTION

The present invention relates to a composition in the form of an ultrafine oil-in-water emulsion which is stabilized by a haloalkynyl derivative and to its uses, in particular in the cosmetics field, as such or in the form of an article containing said composition.

BACKGROUND OF THE INVENTION

For various reasons related in particular to better comfort of use (softness, emollience and others), current cosmetic or dermatological compositions are generally provided in the form of an emulsion of the oil-in-water type (oily phase dispersed in an aqueous phase constituting the continuous phase) or an emulsion of the water-in-oil type (aqueous phase dispersed in an oily phase constituting a continuous phase). Oil-in-water (O/W) emulsions are the most in demand in the field of cosmetics owing to the fact that they contribute to the skin, on application, a softer, less greasy and lighter feel than water-in-oil (W/O) emulsion systems.

Oil-in-water emulsions are generally stabilized by emulsifying surfactants of the oil-in water type which, by virtue of their amphiphilic structure, become positioned at the oily phase/aqueous phase interface and thus stabilize the dispersed oil droplets. Despite the presence of emulsifiers, the emulsions may have a tendency to phase separate (separation of the aqueous and oily phases with release of oil). Increasing the content of emulsifier generally makes it possible to improve the stability of the emulsion. However, the presence of emulsifiers at high concentrations leads to problems of discomfort of the composition obtained when used cosmetically, such as, for example, a rough feel or a sticky or tacky feel, and to irritation problems with respect to the skin, eyes and scalp, as a result of a large amount of surfactants.

In an attempt to solve the problems of stability of conventional O/W emulsions, "ultrafine" O/W emulsions have been proposed in which the mean size of the globules constituting the oily phase is within highly specific limits, namely between 50 and 1000 nm. Such ultrafine O/W emulsions are generally obtained according to a phase-inversion emulsification technique.

This technique is, in its principle, well known to a person skilled in the art and is described in particular in the articles "Phase Inversion Emulsification", by Th. Forster et al., which appeared in Cosmetics & Toiletries, Vol. 106, December 1991, pp. 49–52; and "Application of the phase-inversion-temperature method to the emulsification of cosmetics" by T. Mitsui et al., which appeared in American Cosmetics and Perfumery, Vol. 87, December 1972. The principle of this technique is as follows: a W/O emulsion (introduction of the aqueous phase into the oily phase) is prepared at a temperature which is greater than the phase inversion temperature (PIT) of the system, that is to say the temperature at which the equilibrium between the hydrophilic and lipophilic properties of the emulsifier or emulsifiers employed is reached; at high temperature, that is to say greater than the phase inversion temperature (>PIT), the emulsion is of water-in-oil type and, during its cooling, this emulsion inverts at the phase inversion temperature to become an emulsion of oil-in-water type, this inversion being achieved because the emulsion is previously passed through a microemulsion state.

These ultrafine emulsions are generally extremely fluid. They have a bluish appearance and may be translucent. However, these emulsions are precarious and still present a number of stability problems. In particular, phenomena of creaming and/or of phase separation are observed after several freezing cycles, as well as the appearance of whorls and/or deposits which are difficult to identify.

One of the parameters strongly influencing the stability of O/W emulsions is the size of the dispersed oil droplets, which size is related to the surface tension between the noncontinuous (oily) phase and the continuous (aqueous) phase. The smaller the size of the oil droplets, the lower the surface tension and the greater the stability of the emulsion.

It is known to gel this type of emulsion for the purposes of improving its stability and of widening the range of viscosities, so as to be able to use it in any cosmetic and dermatological field, and of diversifying its textures, in order to adapt them to any skin type.

Unfortunately, the gelling agents commonly used in cosmetics generally have a poor performance in this type of composition. Furthermore, some gelling agents are incompatible with this type of emulsion. Generally, conventional gelling agents do not make it possible to homogeneously thicken emulsions obtained by phase inversion and to stabilize them in different viscosity ranges. In addition, owing to the fact that these gelling agents thicken the compositions, they do not make it possible to obtain compositions having the fluidity desired for certain uses, for example for being used in the form of a spray.

The need thus remains for ultrafine emulsions which can be very fluid while having satisfactory stability. The term "satisfactory stability" is understood to mean that the oil globules remain well distributed in the continuous aqueous phase without phase separation or whorling or deposition or creaming or any other emulsion instability phenomenon occurring.

DETAILED DESCRIPTION OF THE INVENTION

It has been discovered, surprisingly, that the addition of a haloalkynyl derivative makes it possible to obtain a stable ultrafine O/W emulsion. Such stable emulsions are, for example, without the appearance of creaming and without phase separation or deposition, even if the emulsion is very fluid.

The ultrafine O/W emulsions of the present invention possess, in comparison with conventional O/W emulsions, in addition to their greater stability, substantially improved cosmetic properties, such as softness, freshness and comfort on application, as well as a novel feeling of lusciousness and of slip.

The present invention provides a composition for topical application in the form of an oil-in-water emulsion comprising an oily phase dispersed in an aqueous phase, in which the mean size of the oil globules ranges from 50 nm to 1000 nm (nanometers), and a haloalkynyl derivative. Preferably, the composition has a viscosity ranging from 1 to 20 mPa·s at 25° C. This composition preferably constitutes a cosmetic or dermatological composition.

The oil-in-water emulsions of the present invention are capable of being obtained according to the phase-inversion emulsification technique, although it should be recognized that the emulsions can be obtained by any suitable production method yielding O/W emulsions having the desired characteristics.

The compositions of the present invention preferably comprise a physiologically acceptable medium. The term "physiologically acceptable medium" is understood to mean a medium suitable for topical application to the skin or superficial body growths, that is to say compatible with the skin, mucous membranes, lips, hair and nails.

According to preferred embodiments, the present invention makes it possible to obtain very fluid and stable ultrafine emulsions. The term "very fluid" is understood here to mean compositions having a viscosity ranging from 1 to 20 cPoises (1 to 20 mPa·s) and preferably ranging from 1 to 15 cPoises (1 to 15 mPa·s), the viscosity being measured at ambient temperature (25° C.) with a Rheomat RM 180 (generally with the 1 rotor).

Among haloalkynyl derivatives useful in the present invention, 3-iodo-2-propynyl butylcarbamate is known as a fungicide, in particular for wood (see article by Lee et al., Bokin Bobai, 1990, 18(8), p. 365–370). Furthermore, it is described as being an appropriate preservative for cosmetic products by Lonza, which sells it under the name "Glycacil". However, its use or that of other haloalkynyl derivatives for improving the stability of ultrafine emulsions has never been described.

The present invention also provides the use of at least one haloalkynyl derivative as a stabilizing agent for an oil-in-water emulsion in which the mean size of the oil globules ranges from 50 nm to 1000 nm.

According to the present invention, the number-average size of the liquid particles (or globules) of oil (or oily phase) within the dispersing aqueous phase ranges from 50 nm to 1000 nm. Preferably, this mean size ranges from 70 nm to 350 nm and more particularly from 70 nm to 300 nm.

According to preferred embodiments, the compositions according to the present invention possess a very low polydispersity, that is to say that the size of the globules is very homogeneous. As a general rule, 90% of the oil globules of the ultrafine oil-in-water emulsion according to the present invention have a number-average size ranging from 100 to 300 nm. The difference in size between the largest and smallest globules preferably ranges from 20 to 400 nm and more preferably from 30 to 200 nm, whereas, in conventional emulsions (for example, emulsions other than PIT emulsions or microemulsions), the difference in size between the largest and smallest globules is generally greater than 1000 nm.

According to one aspect of the present invention, the haloalkynyl derivative may be selected from, for example, bromoalkynyl or iodoalkynyl alcohol derivatives, such as esters, ethers, acetals, carbamates or carbonates; iodoalkynyl derivatives of pyrimidines, triazolinones, tetrazoles, triazinones, sulphamides, benzothiazoles, ammonium salts, carboxamides, hydroxamates or ureas; and their mixtures.

Preferably, the haloalkynyl derivative is chosen from iodoalkynyl carbamates of formula (I):

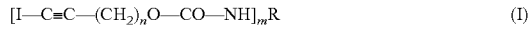

[I—C≡C—(CH$_2$)$_n$O—CO—NH]$_m$R  (I)

in which R is chosen from substituted or unsubstituted alkyl, aryl and aralkyl radicals having from 1 to 20 carbon atoms, m is an integer ranging from 1 to 10, preferably from 1 to 3, and n is an integer ranging from 1 to 10, preferably from 1 to 3.

Preferably, R is an unsubstituted alkyl group comprising from 1 to 20 carbon atoms, more preferably from 1 to 10, and further preferably from 1 to 5 carbon atoms.

According to a preferred embodiment of the present invention, n is equal to 1 and m is equal to 1, and the haloalkynyl derivative is a halopropynyl derivative, preferably iodopropynyl derivative.

Thus, the haloalkynyl derivative may be chosen for example from bromopropargyl or iodopropargyl alcohol derivatives; iodopropargyl derivatives of pyrimidines, triazolinones, tetrazoles, triazinones, sulphamides, benzothiazoles, ammonium salts, carboxamides, hydroxamates or ureas; and their mixtures.

According to a particularly preferred embodiment of the invention, the iodopropynyl derivative is 3-iodo-2-propynyl butylcarbamate.

3-Iodo-2-propynyl butylcarbamate corresponds to the compound of following formula (II):

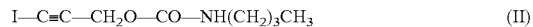

I—C≡C—CH$_2$O—CO—NH(CH$_2$)$_3$CH$_3$  (II)

In the composition according to the present invention, the haloalkynyl derivative and in particular 3-iodo-2-propynyl butylcarbamate can be used as such or in the form of a solution in one or more solvents. For example, suitable solvents can be chosen from esters of a fatty acid and of polyethylene glycol, in particular those comprising from 1 to 20 oxyethylene groups, preferably from 1 to 10 oxyethylene groups; polyethylene glycols of low molecular weight, that is to say with a molecular weight of less than or equal to 450; and their mixtures.

The term "fatty acid" is understood to mean acids comprising from 8 to 26 carbon atoms, preferably from 12 to 22 carbon atoms. The fatty acid ester can derive from a fatty acid or from a mixture of fatty acids, such as the mixture of palmitic, lauric, caprylic and myristic acids resulting from coconut oil. Suitable esters of a fatty acid and of polyethylene glycol include, for example, polyethylene glycol monococoate and dicocoate and in particular those esters comprising 4 oxyethylene groups [polyethylene glycol (4 EO) mono- and dicocoates]; polyethylene glycol monolaurate and dilaurate and in particular those esters comprising 4 oxyethylene groups [polyethylene glycol (4 EO) mono- and dilaurates]; and their mixtures.

Suitable polyethylene glycols with a molecular weight of less than or equal to 450 include, for example, polyethylene glycol (4 EO) or PEG-4, polyethylene glycol (6 EO) or PEG-6, polyethylene glycol (8 EO) or PEG-8 and polyethylene glycol (9 EO) or PEG-9, and their mixtures.

According to preferred embodiments of the present invention, the haloalkynyl derivative used is composed of 3-iodo-2-propynyl butylcarbamate, which is found as a mixture with polyethylene glycol monococoate, polyethylene glycol dicocoate, polyethylene glycol (4 EO) or their mixtures. According to a particularly preferred embodiment of the present invention, the mixture comprising the 4 constituents which is sold by Lonza under the name "Glycacil L" is used. This "Glycacil L" mixture comprises, in addition to 3-iodo-2-propynyl butylcarbamate, polyethylene glycol (4 EO) monococoate, polyethylene glycol (4 EO) dicocoate and PEG-4 in a 10/40/40/10 ratio, that is to say 10% of 3-iodo-2-propynyl butylcarbamate, 40% of polyethylene glycol (4 EO) monococoate, 40% of polyethylene glycol (4 EO) dicocoate and 10% of PEG-4 (CTFA name: PEG-4 laurate, PEG-4 dilaurate, Iodopropynyl carbamate).

The amount of solvent preferably ranges from 0.01 to 20% by weight, more preferably from 0.05 to 10% by weight and most preferably from 0.01 to 5% by weight with respect to the total weight of the composition.

The haloalkynyl derivative and in particular 3-iodo-2-propynyl butylcarbamate can also be used in the composition according to the present invention in the solid form, as such or as a mixture, in particular as a mixture with an alkali metal or alkaline earth metal carbonate or bicarbonate, preferably sodium bicarbonate.

The amount of haloalkynyl derivative in the composition of the present invention must be sufficient to produce the desired stability. In practice, the amount of haloalkynyl derivative preferably ranges from 0.001 to 10% by weight of active material, more preferably from 0.005 to 5% by weight of active material, further preferably from 0.01 to 1% by weight of active material and also further preferably from 0.01 to 0.5% by weight of active material with respect to the total weight of the composition.

The nature of the oily phase in the composition of the emulsions according to the present invention is not critical. Thus, the oily phase can be composed of any compound which is suitable for the manufacture of emulsions of oil-in-water type in the cosmetics field or dermatological field. In particular, these compounds can be chosen, alone or as mixtures, from oils of vegetable, animal or mineral origin, natural or synthetic waxes, and various other fatty substances, it being necessary for these oils, in particular cosmetic oils, and other fatty substances to be physiologically acceptable.

The oily phase usually comprises at least one oil. Useful oils include:

mineral oils, such as liquid paraffin and liquid petrolatum;
hydrocarbonaceous oils of animal origin, such as perhydrosqualene;
hydrocarbonaceous oils of vegetable origin, such as sweet almond oil, avocado oil, castor oil, coriander oil, olive oil, jojoba oil, sesame oil, groundnut oil, grape seed oil, rapeseed oil, coconut oil, hazelnut oil, karite butter, palm oil, apricot kernel oil, calophyllum oil, rice bran oil, maize germ oil, wheat germ oil, soybean oil, sunflower oil, evening primrose oil, safflower oil, passion flower oil, rye oil, or triglycerides of caprylic/capric acids, such as those sold by Stearineries Dubois or those sold under the names Miglyol 810, 812 and 818 by Dynamit Nobel;
synthetic oils, such as purcellin oil, butyl myristate, isopropyl myristate, cetyl myristate, isopropyl palmitate, 2-ethylhexyl palmitate, isopropyl adipate, ethylhexyl adipate, butyl stearate, hexadecyl stearate, isopropyl stearate, octyl stearate, isocetyl stearate, decyl oleate, hexyl laurate, propylene glycol dicaprylate and the esters derived from lanolic acid, such as isopropyl lanolate or isocetyl lanolate, dioctylcyclohexane, isoparaffins and poly-α-olefins.

Other oils which can be used in the emulsions according to the present invention include ethers, such as dicaprylyl ether (CTFA name: Dicaprylyl ether); benzoates of $C_{12}$–$C_{15}$ fatty alcohols (Finsolv TN from Finetex); fatty alcohols comprising from 8 to 26 carbon atoms, such as lauryl alcohol, cetyl alcohol, myristyl alcohol, stearyl alcohol, palmityl alcohol, oleyl alcohol, linoleyl alcohol, 2-octyldodecanol, and their mixtures, such as cetearyl alcohol (mixture of cetyl alcohol and of stearyl alcohol); acetylglycerides; octanoates and decanoates of alcohols and of polyalcohols, such as those of glycol and of glycerol; ricinoleates of alcohols and of polyalcohols, such as those of cetyl alcohol; fluorinated and perfluorinated oils; lanolin; hydrogenated lanolin; acetylated lanolin; and volatile or nonvolatile silicone oils, such as volatile or nonvolatile polymethylsiloxanes (PDMS) with a linear or cyclic silicone chain which are liquid or pasty at ambient temperature, in particular cyclopolydimethylsiloxanes (cyclomethicones), such as cyclohexasiloxane; polydimethylsiloxanes comprising pendent alkyl, alkoxy or phenyl groups or alkyl, alkoxy or phenyl groups at the end of the silicone chain, which groups have from 2 to 24 carbon atoms; or phenylated silicones, such as phenyl trimethicones, phenyl dimethicones, phenyltrimethylsiloxydiphenyl-siloxanes, diphenyl dimethicones, diphenylmethyldiphenyltrisiloxanes, (2-phenylethyl)trimethylsiloxysilicates or polymethylphenylsiloxanes.

The term "hydrocarbonaceous oil" in the list of the oils which are mentioned above is understood to mean any oil predominantly comprising carbon and hydrogen atoms and optionally ester, ether, fluorinated, carboxylic acid and/or alcohol groups.

Use may be made of one oil or a mixture of several of oils such as those exemplified above.

According to a preferred embodiment of the present invention, the composition comprises at least one oil of vegetable origin, for example palm oil, or at least one mineral oil, such as liquid petrolatum, or a mixture of at least one mineral oil and of at least one vegetable oil.

According to another preferred embodiment of the present invention, the composition comprises at least one emollient chosen from the oils indicated above, preferably dicaprylyl ether, dioctylcyclohexane, or their mixtures.

Conventionally, the aqueous phase can comprise, in addition to water, one or more water-soluble solvents. Suitable solvents can be chosen from polyols (or polyhydric alcohols), water-soluble lower alcohol(s), and their mixtures. The term "lower alcohol" is understood to mean an alcohol comprising from 1 to 8 carbon atoms. Suitable polyols include, for example, glycerol; glycols, such as propylene glycol or butylene glycol; sorbitol; sugars, such as glucose, fructose, maltose, lactose or sucrose; and their mixtures. Suitable lower alcohols include, for example, ethanol, isopropanol, butanol and their mixtures.

The oil-in-water emulsions in accordance with the present invention preferably comprise:
(i) from 50 to 95% by weight, more preferably from 70 to 90% by weight, of aqueous phase with respect to the total weight of the composition;
(ii) from 5 to 50% by weight, more preferably from 10 to 30% by weight, of oily phase with respect to the total weight of the composition.

In addition, the emulsions in accordance with the present invention may comprise one or more emulsifying surfactants, the use of which is generally necessary for the preparation and the production of the ultrafine emulsion. In addition, they can comprise specific coemulsifiers, the role of which is, for example, to substantially reduce the amount of emulsifying surface-active agents necessary for the preparation of the emulsion during the preparation of the emulsion.

The emulsifiers which can be used in the present invention are preferably chosen from nonionic compounds composed, on the one hand, of a lipophilic residue chosen, for example, from $C_6$–$C_{30}$ alkyl or acyl functional groups and, on the other hand, of a hydrophilic residue chosen, for example, from polyol groups (glycerol, glycol, glucose) and polyol ethers. Their HLB (Hydrophilic Lipophilic Balance) balance preferably ranges from 9 to 18, more preferably from 9.5 to 11.5.

Suitable nonionic emulsifiers used in the present invention include the addition products of ethylene oxide with fatty alcohols having 6 to 30 carbon atoms or with partial esters of polyols having 3 to 16 carbon atoms 17 and of fatty acids having 14 to 22 carbon atoms, and their mixtures.

Thus, for example, suitable addition products of ethylene oxide with fatty alcohols include an emulsifier corresponding to the formula (III):

$$R-(O-CH_2-CH_2)_n-OH \qquad (III)$$

in which R represents a saturated or unsaturated and linear or branched hydrocarbonaceous residue having from 8 to 30 carbon atoms and n represents a number ranging from 8 to 50, preferably from 8 to 30. Suitable addition products of ethylene oxide with behenyl alcohol include, for example, Beheneth-9 (9 mol of ethylene oxide) and Beheneth-10 (10 mol of ethylene oxide); those obtained with cetyl alcohol or with stearyl alcohol or with their mixtures, in particular those comprising 12 to 20 mol of ethylene oxide, such as, for example, those obtained from the mixture of cetyl alcohol and of stearyl alcohol (cetearyl alcohol), such as Ceteareth-12, Ceteareth-13, Ceteareth-14, Ceteareth-15, Ceteareth-16, Ceteareth-17, Ceteareth-18 or Ceteareth-20; those obtained from cetyl alcohol, such as Ceteth-14, Ceteth-15, Ceteth-16 or Ceteth-20; those obtained from stearyl alcohol, such as Steareth-13, 18 Steareth-14, Steareth-15, Steareth-16 or Steareth-20, and the mixtures of these various emulsifiers.

The addition products of ethylene oxide with partial esters of polyols and of fatty acids can be obtained by ethoxylation of glycerol partial esters of fatty acids or of sorbitol mono- or diesters of fatty acids. Use may be made, for example, of the addition products of 4 to 20 mol of ethylene oxide with one or more glycerol partial esters. The term "glycerol partial esters" is understood to mean, for example, the mixtures of mono-, di- and triglycerides of $C_{10}$–$C_{20}$ fatty acids obtained by esterification of one mole of glycerol by 1 or 2 mol of a $C_{10}$–$C_{20}$ fatty acid.

In addition, the emulsions according to the present invention can furthermore comprise one or more coemulsifiers. This or these coemulsifiers can be chosen, for example, from $C_{16}$–$C_{22}$ fatty alcohols or esters of $C_3$–$C_6$ polyols with $C_{14}$–$C_{22}$ fatty acids, and their mixtures. Suitable coemulsifiers include, for example, cetyl alcohol, stearyl alcohol, cetearyl alcohol (mixture of cetyl alcohol and of stearyl alcohol), glyceryl stearate, and their mixtures.

Use may be made, for example, as mixture comprising emulsifier and coemulsifier, of the mixture sold under the name Emulgade SEV by Cognis, comprising Ceteareth-20, Ceteareth-12, hydrogenated palm oil and cetearyl alcohol.

The amount of emulsifiers and of coemulsifiers in the composition of the present invention generally ranges from 0.05 to 30% by weight, preferably from 0.5 to 20% by weight and more preferably from 2 to 10% by weight with respect to the total weight of the composition.

The composition according to the present invention can also comprise any adjuvant or additive commonly used in the fields under consideration and in particular in the cosmetics field or dermatological field.

Suitable conventional adjuvants in the aqueous phase and/or in the oily phase of the emulsions in accordance with the invention (according to the water-soluble or fat-soluble nature of these adjuvants) include ionic or nonionic gelling agents and thickening agents; hydrophilic or lipophilic cosmetic or dermatological active principles; fragrances; preservatives; sequestering agents (EDTA); pigments; pearlescence agents; inorganic or organic fillers, such as talc, kaolin, silica powder or polyethylene powder; soluble dyes; sunscreen agents; basifying or acidifying agents; and their mixtures. The amounts of these various adjuvants are those conventionally used in the field under consideration, for example from 0.01 to 20% of the total weight of the composition.

According to a preferred embodiment of the present invention, the composition according to the invention additionally comprises polyhexamethylene biguanide (CTFA name: polyaminopropyl biguanide) hydrochloride. This compound is a preservative exhibiting the advantage of fully complementing, by its bactericidal effectiveness, the fungicidal effectiveness of iodopropynyl butylcarbamate, to thus produce the best possible microbiological protection of the composition. Polyhexamethylene biguanide hydrochloride, if present, is present in the composition of the invention in an amount sufficient to act as preservative. Thus, this compound is present in an amount ranging, for example, from 0.001 to 5% of the total weight of the composition, preferably from 0.005 to 2% of the total weight of the composition and more preferably from 0.01 to 1% of the total weight of the composition.

Furthermore, the composition according to the present invention can comprise one or more active principles, and the cosmetic or dermatological active principles which can be used depend on the purpose of this composition. Suitable active principles include, for example, bactericides, such as octopirox, triclosan and triclocarban; keratolytic and anti-aging agents, such as hydroxy acids (α-hydroxy acids and β-hydroxy acids), for example lactic acid, glycolic acid, citric acid, salicylic acid and their derivatives; essential oils; vitamins and in particular retinol (vitamin A), ascorbic acid (vitamin C), tocopherol (vitamin E), niacinamide (vitamin PP or B3), panthenol (vitamin B5) and their derivatives (for example esters); coenzymes and in particular coenzyme Q10 or ubiquinone; enzymes, such as, for example, lipases, proteases, phospholipases, cellulases, peroxidases, in particular lactoperoxidases, catalases or superoxide dismutases, and plant extracts comprising the abovementioned enzymes; yeasts, such as *Saccharomyces cerevisiae*; steroids; antioxidants and agents for combating free radicals; moisturizing agents, such as polyols (glycerol, sorbitol, sugars), protein hydrolysates, urea and the mixtures comprising them; slimming agents, such as caffeine; antielastase and anticollagenase agents; agents for the treatment of greasy skin; and their mixtures.

Suitable salicylic acid derivatives include 5-(n-octanoyl) salicylic acid (CTFA name: Capryloyl Salicylic Acid), 5-(ndecanoyl)salicylic acid, 5-(n-dodecanoyl)salicylic acid, 5-(n-octyl)salicylic acid, 5-(nheptyloxy)salicylic acid, 5-(tert-octyl)salicylic acid, 5-butoxysalicylic acid, 5-ethoxysalicylic acid, 5-methoxysalicylic acid, 5-propoxysalicylic acid, 5-methylsalicylic acid, 5-ethylsalicylic acid, 5-propylsalicylic acid, and their mixtures. These acids can optionally be salified by a base.

Suitable steroids include, for example, dehydroepiandrosterone (or DHEA), as well as (1) its biological derivatives and precursors, in particular DHEA salts and esters, such as DHEA sulphate and salicylate, 7-hydroxy-DHEA, 7-keto-DHEA, or esters of 7-hydroxy- and 7-keto-DHEA, in particular 3-β-acetoxy-7-oxo-DHEA, and (2) its chemical derivatives and precursors, in particular sapogenins, such as diosgenin or hecogenin, and/or their derivatives, such as hecogenin acetate, and/or the natural extracts comprising them and in particular extracts of Dioscorea species, such as wild yam.

The sunscreen agents (or UV screening agents) optionally present in the composition can be chosen from organic screening agents, physical screening agents and their mixtures.

The composition of the present invention can comprise, as chemical sunscreen agents which can be used in the composition of the invention, any UV-A and UV-B screening agent which can be used in the cosmetics field.

Suitable UV-B screening agents include, for example:
(1) salicylic acid derivatives, in particular homomenthyl salicylate and octyl salicylate;
(2) cinnamic acid derivatives, in particular 2-ethylhexyl p-methoxycinnamate, sold by Givaudan under the name Parsol MCX;
(3) liquid β,β-diphenylacrylate derivatives, in particular 2-ethylhexyl α-cyano-β,β-iphenylacrylate or octocrylene, sold by BASF under the name Uvinul N539;
(4) p-aminobenzoic acid derivatives;
(5) 4-methylbenzylidenecamphor, sold by Merck under the name Eusolex 6300;
(6) 2-phenylbenzimidazole-5-sulphonic acid, sold under the name Eusolex 232 by Merck;
(7) 1,3,5-triazine derivatives, in particular:
   2,4,6-tris[p-(2'-ethylhexyl-1'-oxycarbonyl)anilino]-1,3,5-triazine, sold by BASF under the name Uvinul T150, and
   dioctylbutamidotriazone, sold by Sigma 3V under the name Uvasorb HEB; and
(8) the mixtures of these screening agents.

Suitable UV-A screening agents include, for example:
(1) dibenzoylmethane derivatives, in particular 4-(tert-butyl)-4'-methoxydibenzoylmethane, sold by Givaudan under the name Parsol 1789;
(2) benzene-1,4-[di(3-methylidenecamphor-10-sulphonic acid)], optionally in the partially or completely neutralized form, sold under the name Mexoryl SX by Chimex;
(3) benzophenone derivatives, for example:
   2,4-dihydroxybenzophenone (benzophenone-1);
   2,2',4,4'-tetrahydroxybenzophenone (benzophenone-2);
   2-hydroxy-4-methoxybenzophenone (benzophenone-3), sold under the name Uvinul M40 by BASF;
   2-hydroxy-4-methoxybenzophenone-5-sulphonic acid (benzophenone-4) and its sulphonate form (benzophenone-5), sold by BASF under the name Uvinul MS40;
   2,2'-dihydroxy-4,4'-dimethoxybenzophenone (benzophenone-6);
   5-chloro-2-hydroxybenzophenone (benzophenone-7);
   2,2'-dihydroxy-4-methoxybenzophenone (benzophenone-8);
   the disodium salt of 2,2'-dihydroxy-4,4'-dimethoxybenzophenone-5,5'-disulphonic diacid (benzophenone-9);
   2-hydroxy-4-methoxy-4'-methylbenzophenone (benzophenone-10);
   benzophenone-11;
   2-hydroxy-4-(octyloxy)benzophenone (benzophenone-12);
(4) silane derivatives or polyorganosiloxanes comprising a benzophenone group;
(5) anthranilates, in particular menthyl anthranilate, sold by Haarmann & Reimer under the name Neo Heliopan MA;
(6) compounds comprising, per molecule, at least two benzazolyl groups or at least one benzodiazolyl group, in particular 1,4-bis(benzimidazolyl)phenylene-3,3',5,5'-tetrasulphonic acid and its salts, sold by Haarmann & Reimer;
(7) silicon derivatives of N-substituted benzimidazolyl-benzazoles or of benzofuranylbenzazoles, and in particular:
   2-[1-[3-[1,3,3,3-tetramethyl-1-[(trimethylsilyl)oxy]disiloxanyl]propyl]-1Hbenzimidazol-2-yl]benzoxazole;
   2-[1-[3-[1,3,3,3-tetramethyl-1-[(trimethylsilyl)oxy]disiloxanyl]propyl]-1Hbenzimidazol-2-yl]benzothiazole;
   2-[1-(3-(trimethylsilanyl)propyl)-1H-benzimidazol-2-yl]benzoxazole;
   6-methoxy-1,1'-bis(3-(trimethylsilanyl)propyl)-1H,1'H-[2,2']bibenzimidazolyl-benzoxazole;
   2-[1-(3-(trimethylsilanyl)propyl)-1H-benzimidazol-2-yl]benzothiazole;
   which are disclosed in Patent Application EP-A-1 028 120;
(8) triazine derivatives and in particular 2,4-bis[4-(2-ethylhexyloxy)-2-hydroxyphenyl]-6-(4-methoxyphenyl)-1,3,5-triazine, sold by Ciba Geigy under the name Tinosorb S, and 2,2'-methylenebis[6-(2H-benzotriazol-2-yl)-4-(1,1,3,3-tetramethylbutyl)phenol], sold by Ciba Geigy under the name Tinosorb M;
(9) their mixtures.

It is also possible to use a mixture of several of these screening agents and a mixture of UV-B screening agents and of UV-A screening agents and also mixtures with physical screening agents. Suitable physical screening agents include titanium oxide (amorphous titanium dioxide or crystalline titanium dioxide in the rutile and/or anatase form), zinc oxide, iron oxide, zirconium oxide, cerium oxide or their mixtures. These metal oxides can be in the form of particles having a micrometric size or nanometric size (nanopigments). In the form of nanopigments, the mean sizes of the particles range, for example, from 5 to 100 nm. Nanopigments are preferably used in the composition of the invention.

Of course, a person skilled in the art will take care to choose the possible compound or compounds to be added to the composition according to the invention so that the advantageous properties intrinsically attached to the composition in accordance with the present invention are not, or not substantially, detrimentally affected by the envisaged addition.

Although the emulsions according to the invention can be obtained through any method which yields emulsions having the desired characteristics, the emulsions are preferably obtained by a phase inversion process. This preparation process is characterized in that:
1) (A) the oily phase, this oily phase comprising at least one oil and optionally other oils and fatty substances and the fat-soluble adjuvants which are stable at the phase inversion temperature,
(B) at least one emulsifier and optionally a coemulsifier, and
(C) the aqueous phase, this aqueous phase comprising water and optionally the water-soluble solvents and the water-soluble adjuvants which are stable at the phase inversion temperature, are mixed in order to produce a conventional emulsion,
(2) this emulsion is heated to a temperature situated within or above the phase inversion region, or else the emulsion is prepared directly at such a temperature, then
(3) the emulsion is cooled and the haloalkynyl derivative and optionally the adjuvants or active principles which are unstable at the phase inversion temperature, such as, for example, fragrances, are added.

The phase inversion temperature region is established for a given composition by measuring the conductivity of a sample of the composition which is heated. When the phase inversion region is reached, the conductivity of the emulsion increases very rapidly: for example, in the phase inversion region, an increase in the conductivity of approximately 50 microsiemens per centimetre may be observed over a temperature range of 5 to 15° C., whereas it would only be approximately 5 microsiemens per centimetre over an equivalent temperature range outside the phase inversion region.

The compositions according to the present invention can be provided in the form of a lotion or milk or in the form of a fluid cream. They can be used as such or as an aerosol or in the form of a spray. According to a preferred embodiment of the present invention, the composition is provided in the form of a very fluid emulsion of lotion or milk type and it is preferably used in the form of a spray. As indicated above, the very fluid emulsions are those having a viscosity ranging from 1 to 20 cPoises (1 to 20 mPa·s), the viscosity being measured at ambient temperature (approximately 25° C.) with a Rheomat RM 180 (generally with the 1 rotor).

The compositions of the present invention can constitute care, protection and/or hygiene products for the skin of the face and/or of the body, the hair, the scalp, eyelashes, eyebrows, nails or mucous membranes, such as protective, treatment or care sprays for the face, for the hands or for the body, or body milks or lotions for protection or care of the skin, scalp or mucous membranes or for removing make-up from and/or cleaning the skin, lips and/or hair. They can be used, for example, for moisturizing and/or firming up the skin and/or for nourishing the skin.

The compositions according to the present invention can also constitute hair products, antisun products, for protecting the skin of the body and/or of the face or the hair from the harmful effects of the sun or UV radiation, and also products for making up keratinous substances and in particular the skin, lips, and/or eyelashes.

Thus, present invention provides for the cosmetic use of the composition as defined above for treating, protecting, caring for, removing make-up from and/or cleaning the skin, lips and/or hair and/or for making up the skin and/or lips.

The present invention further provides a process for the cosmetic treatment of the skin, including the scalp, the hair, the eyebrows, the nails and/or the lips, comprising applying a composition as defined above to the skin, the hair, the eyebrows, the nails and/or the lips. The type of treatment can vary in particular as a function of the active principle or principles present in the composition.

According to another embodiment of the present invention, articles containing the compositions according to the present invention can be prepared. For example, the compositions of the present invention can be used for impregnating a water-insoluble substrate in order to form an article to be applied to the skin, such as a wipe. The water-insoluble substrate can be chosen from the group consisting of woven 30 materials, nonwoven materials, foams, sponges and waddings, as sheets, balls or films. It can in particular be a nonwoven substrate based on fibres of natural origin (linen, wool, cotton, silk) or of synthetic origin (cellulose derivatives, viscose, polyvinyl derivatives, polyesters, such as poly(ethylene) terephthalate, polyolefins, such as polyethylene or polypropylene, polyamides, such as Nylon, or acrylic derivatives). Nonwovens are described in a general way in Riedel, "Nonwoven Bonding Methods & Materials", Nonwoven World (1987). These substrates are obtained according to conventional processes in the art of preparing nonwovens. According to a specific embodiment of the present invention, the insoluble substrate can comprise a compound, for example, a preservative, which is attached to the support by known means for grafting biocidal agents to fibres.

This substrate can comprise one or more layers having identical or different properties and can have properties of elasticity and of softness and other properties appropriate for the desired use. The substrates can comprise, for example, two parts having different properties of elasticity, as disclosed in the document WO-A-99/13861, or can comprise a single layer with different densities, as disclosed in the document WO-A-99/25318, or can comprise two layers of different textures, as disclosed in the document WO-A-98/18441.

The substrate can have any size and any shape appropriate for the desired purpose. It preferably has a surface area of between 0.005 $m^2$ and 0.1 $m^2$, preferably between 0.01 $m^2$ and 0.05 $m^2$. It is preferably provided in the form of rectangular wipes or of round compresses.

The final article comprising the substrate and the composition of the present invention is preferably in the wet state, with a degree of impregnation of the composition ranging, for example, from 200 to 1000%, preferably from 250 to 350% by weight of composition with respect to the weight of substrate. Techniques for impregnating substrates with compositions are well known in this field and are all applicable to the present invention. In general, the impregnation composition is added to the substrate by one or more techniques comprising immersion, coating, vaporization, and the like.

However, it is also possible to form a dry article (or wipe), for example by removing the water from the composition after its impregnation on the substrate or by impregnating the substrate with a composition in dry form in the powder, granule or film state by any known implementation means such as, for example, welding and bonding of multilayers by thermal or ultrasound routes. In the latter embodiment, the composition is dried by any known means: for example, atomization, lyophilization or other analogous process.

It is thus possible to obtain, according to the use envisaged, wet wipes or dry wipes. The wet wipes can be used as such, whereas the dry wipes are wetted before use.

The present invention thus provides an article comprising (A) a water-insoluble substrate, and (B) a composition as defined above, added to or impregnated on the substrate, and the uses of the said article in the cosmetics or dermatological field, in particular for caring for (nourishing, firming up, moisturizing), cleaning and/or removing make-up from the skin.

This article can constitute in particular wipes for caring for and/or treating the skin and/or wipes for cleaning and/or removing make-up from the skin and/or eyes.

The present invention also provides a cosmetic process for caring for, cleaning and/or removing make-up from the skin, which comprises passing an article as defined above over the skin.

The examples indicated below will make possible a better understanding of the invention without, however, exhibiting a limiting nature. The amounts shown are as % by weight, unless otherwise mentioned. The names are chemical names and CTFA names, according to the compounds.

EXAMPLE 1

Very Fluid Milk

| Phase A | |
|---|---|
| Mineral oil | 5% |
| Dicaprylyl ether (Cetiol OE from Cognis) | 3% |

-continued

| | |
|---|---|
| Mixture of Ceteareth-20, Ceteareth-12, hydrogenated palm oil and cetearyl alcohol (Emulgade SEV from Cognis) | 3% |
| Ceteareth-20 (Emulgin B2 from Cognis) | 1% |
| Phase B | |
| Glycerol | 5% |
| Distilled water | 15% |
| Phase C | |
| Palm oil | 1% |
| Fragrance | 0.3% |
| Phase D | |
| Glycacil L (sold by Lonza) (i.e. 0.02% of 3-iodo-2-propynyl butylcarbamate) | 0.2% |
| Distilled water | q.s. for 100% |

Procedure:

Phases A and B are heated to 70° C. and are homogenized. Phase B is poured slowly onto phase A with slow stirring and the mixture is heated as far as the phase inversion temperature (PIT), which is in the vicinity of 80° C. The water-in-oil emulsion obtained becomes virtually transparent and very bluish. Heating is halted and phase C is poured into the emulsion while retaining slow stirring. After cooling to ambient temperature (20 to 25° C.), the emulsion has inverted and phase D is added with slow stirring.

An oil-in-water emulsion is obtained which is very fluid (fluid as water, viscosity of approximately 1 mPa·s) and slightly bluish, which emulsion can be used as a spray or can be impregnated on a nonwoven support to form a wipe to be applied to the face or the body for the purpose, for example, of nourishing, moisturizing and firming up the skin.

EXAMPLE 2

Milky Lotion

| | |
|---|---|
| Phase A | |
| Mineral oil | 5% |
| Dicaprylyl ether (Cetiol OE from Cognis) | 3% |
| Mixture of Ceteareth-20, Ceteareth-12, hydrogenated palm oil and cetearyl alcohol (Emulgade SEV from Cognis) | 3% |
| Ceteareth-20 (Emulgin B2 from Cognis) | 1% |
| Phase B | |
| Glycerol | 5% |
| Distilled water | 15% |
| Phase C | |
| Palm oil | 0.5% |
| Fragrance | 0.5% |
| Phase D | |
| Glycacil L (from Lonza) (i.e. 0.02% of 3-iodo-2-propynyl butylcarbamate) | 0.2% |
| Polyhexamethylene biguanide hydrochloride | 0.5% |
| Distilled water | q.s. for 100% |

The procedure is the same as for Example 1.

An oil-in-water emulsion is obtained which is very fluid (like milk) and slightly bluish, which emulsion can be used as a spray or can be impregnated on a support to form a wipe to be applied to the face or the body.

The invention claimed is:

1. A composition in the form of an oil-in-water emulsion comprising
at least one additive selected from the group consisting of gelling agents, thickening agents, hydrophilic or lipophilic active principles, fragrances, preservatives, sequestering agents, pigments, pearlescence agents, fillers, soluble dyes, sunscreen agents, basifying agents, acidifying agents, and mixtures thereof,
an oily phase dispersed in an aqueous phase, in which the mean size of the oil globules ranges from 50 nm to 1000 nm, and a haloalkynyl compound present in an amount sufficient to stabilize the oil-in-water emulsion, wherein the composition has a viscosity of from 1 to 20 cP at 25° C. and is prepared through phase-inversion emulsification,
wherein the haloalkynyl compound is selected from the group consisting of bromopropargyl alcohol derivatives, iodopropargyl alcohol derivatives, iodopropargyl derivatives of pyrimidines, iodopropargyl derivatives of triazolinones, iodopropargyl derivatives of tetrazoles, iodopropargyl derivatives of triazinones, iodopropargyl derivatives of sulphamides, iodopropargyl derivatives of benzothiazoles, iodopropargyl derivatives of ammonium salts, iodopropargyl derivatives of carboxamides, iodopropargyl derivatives of hydroxamates, iodopropargyl derivatives of ureas, and mixtures thereof, and
wherein the oily phase comprises at least one oil selected from the group consisting of mineral oils, hydrocarbonaceous oils of animal origin, hydrocarbonaceous oils of vegetable origin, synthetic oils, ethers, benzoates of $C_{12}$–$C_{15}$ fatty alcohols, fatty alcohols comprising from 8 to 26 carbon atoms, acetylglycerides, octanoates and decanoates of alcohols and of polyalcohols, ricinoleates of alcohols and of polyalcohols, fluorinated and perfluorinated oils, lanolin, hydrogenated lanolin, acetylated lanolin, silicone oils, and mixtures thereof.

2. The composition according to claim 1, wherein the mean size of the oil globules ranges from 70 nm to 350 nm.

3. The composition according to claim 1, wherein 90% of the oil globules have a size ranging from 100 to 300 nm and the difference in size between the largest and the smallest particles ranges from 20 to 400 nm.

4. The composition according to claim 1, wherein the haloalkynyl compound is a bromopropargyl alcohol derivative or iodopropargyl alcohol derivative selected from the group consisting of bromopropargyl alcohol ethers, bromopropargyl alochol acetals, bromopropargyl alcohol carbamates, bromopropargyl alcohol carbonates, iodopropargyl alcohol ethers, iodopropargyl alcohol acetals, iodopropargyl alcohol carbamates and iodopropargyl alcohol carbonates.

5. The composition according to claim 4, wherein the haloalkynyl compound is a iodoalkynyl carbamate of formula (I):

$$[I-C\equiv C-CH_2)_nO-CO-NH]_mR \qquad (I)$$

in which R is substituted or unsubstituted alkyl, aryl or aralkyl radical having from 1 to 20 carbon atoms, m is an integer ranging from 1 to 10 and n is an integer ranging from 1 to 10.

6. The composition according to claim 5, wherein n is 1 and m is 1.

7. The composition according to claim 5, wherein R is an unsubstituted alkyl group comprising from 1 to 20 carbon atoms.

8. The composition according to claim 5, wherein R is an unsubstituted alkyl group comprising from 1 to 10 carbon atoms.

9. The composition according to claim 1, wherein the haloalkynyl compound is 3-iodo-2-propynyl butylcarbamate.

10. The composition according to claim 1, wherein the composition further comprises a solvent selected from the group consisting of esters of a fatty acid and of polyethylene glycol, polyethylene glycols with a molecular weight of less than or equal to 450, and mixtures thereof.

11. The composition according to claim 10, wherein the solvent is selected from the group consisting of PEG-4, PEG-6, PEG-8, PEG-9, polyethylene glycol (4 EO) mono- and dicocoates, polyethylene glycol (4 EO) mono- and dilaurates, and mixtures thereof.

12. The composition according to claim 9, wherein the composition further comprises polyethylene glycol (4 EO) monococoate, polyethylene glycol (4 EO) dicocoate and PEG-4.

13. The composition according to claim 1, wherein the haloalkynyl compound is in solid form as a mixture with an alkali metal or alkaline earth metal carbonate or bicarbonate.

14. The composition according to claim 13, wherein the solid haloalkynyl compound is selected from the group consisting of haloalkynyl compound, haloalkynyl compound in mixture with an alkali metal and haloalkynyl compound in mixture with alkaline earth metal carbonate or bicarbonate.

15. The composition according to claim 1, wherein the amount of haloalkynyl compound ranges from 0.001 to 10% by weight of active material with respect to the total weight of the composition.

16. The composition according to claim 1, wherein the amount of haloalkynyl compound ranges from 0.005 to 5% by weight of active material with respect to the total weight of the composition.

17. The composition according to claim 1, wherein the oily phase comprises at least one oil selected from the group consisting of mineral oil, vegetable oil, and a mixture thereof.

18. The composition according to claim 1, wherein the oily phase comprises at least one emollient selected from the group consisting of dicaprylyl ether, dioctylcyclohexane, and mixtures thereof.

19. The composition according to claim 1, wherein the aqueous phase comprises at least one water-soluble solvent selected from the group consisting of polyols, water-soluble alcohols comprising from 1 to 8 carbon atoms, and mixtures thereof.

20. The composition according to claim 1, wherein the aqueous phase represents from 50 to 95% by weight with respect to the total weight of the composition.

21. The composition according to claim 1, wherein the aqueous phase represents from 70 to 90% by weight with respect to the total weight of the composition.

22. The composition according to claim 1, wherein the oily phase represents from 5 to 50% by weight with respect to the total weight of the composition.

23. The composition according to claim 1, wherein the oily phase represents from 10 to 30% by weight with respect to the total weight of the composition.

24. The composition according to claim 1, wherein the composition comprises at least one nonionic emulsifier comprising a lipophilic residue selected from the group consisting of $C_6$–$C_{30}$ alkyl and acyl functional groups, and a hydrophilic residue selected from the group consisting of polyol groups and polyol ethers.

25. The composition according to claim 24, wherein the emulsifier exhibits an HLB balance ranging from 9 to 18.

26. The composition according to claim 24, wherein the emulsifier is selected from the group consisting of:
(a) the compounds corresponding to the formula (III):

$$R\text{—}(O\text{—}CH_2\text{—}CH_1)_n\text{—}OH \qquad (III)$$

in which R represents a saturated or unsaturated and linear or branched hydrocarbonaceous residue having from 8 to 28 carbon atoms and n represents a number ranging from 8 to 50;
(b) the addition products of 4 to 20 mol of ethylene oxide with one or more glycerol partial esters; and
(c) mixtures thereof.

27. The composition according to claim 26, wherein the emulsifier is an addition product of ethylene oxide with an alcohol selected from the group consisting of behenyl alcohol, cetyl alcohol, stearyl alcohol, and mixtures thereof.

28. The composition according to claim 1, wherein the composition further comprises a coemulsifier selected from the group consisting of $C_{16}$–$C_{22}$ fatty alcohols, partial esters of $C_3$–$C_6$ polyols with $C_{14}$–$C_{22}$ fatty acids, and mixtures thereof.

29. The composition according to claim 28, wherein the coemulsifier is selected from the group consisting of cetyl alcohol, stearyl alcohol, cetearyl alcohol, glyceryl stearate, and mixtures thereof.

30. The composition according to claim 24, wherein the amount of emulsifiers and of coemulsifiers generally ranges from 0.05 to 30% by weight, with respect to the total weight of the composition.

31. The composition according to claim 24, wherein the amount of emulsifiers and of coemulsifiers generally ranges from 0.5 to 20% by weight, with respect to the total weight of the composition.

32. The composition according to claim 1, wherein the composition further comprises polyhexamethylene biguanide hydrochloride.

33. The composition according to claim 32, wherein the polyhexamethylene biguanide hydrochloride is present in an amount ranging from 0.00 1 to 5% of the total weight of the composition.

34. The composition according to claim 1, wherein the composition comprises one or more active principles selected from the group consisting of bactericides, keratolytic agents, essential oils, vitamins, coenzymes, enzymes, yeasts, steroids, antioxidants and agents for combating free radicals, moisturizing agents, slimming agents, antielastase and anticollagenase agents, agents for treating greasy skin, and mixtures thereof.

35. The composition according to claim 1, wherein the composition is a cosmetic or dermatological composition.

36. A method for treating, protecting, caring for, removing make-up from and/or cleaning the skin, lips and/or hair comprising applying the composition according to claim 1 to skin, lips and/or hair.

37. A method for making up the skin and/or lips comprising applying the composition according to claim 1 to skin and/or lips.

38. The composition according to claim 1, wherein the composition further comprises a sunscreen agent.

39. A process for treating the skin, hair, eyebrows, nails and/or lips, comprising applying the composition of claim 1 to the skin, the hair, eyebrows, nails and/or lips.

40. A process for preparing a composition according to claims 1 comprising producing a conventional water-in-oil emulsion, ensuring that the emulsion is at a temperature within or above the phase inversion region, and cooling the emulsion.

41. An article comprising (A) a water-insoluble substrate and (B) a composition according to claim 1.

42. The article according to claim 41, wherein the composition according to claim 1 is added to the substrate.

43. The article according to claim 41, wherein the composition according to claim 1 is impregnated on the substrate.

44. The article according to claim 41, wherein the substrate is selected from the group consisting of woven materials, nonwoven materials, foams, sponges and waddings.

45. The article according to claim 41, wherein the substrate is a nonwoven substrate based on fibres of natural origin or of synthetic origin.

46. The article according to claim 41, wherein the article comprises from 200 to 1000% by weight of composition with respect to the weight of substrate.

47. The article according to claim 41, wherein the article is in the form of rectangular wipes or of round compresses.

48. A method for caring for and/or treating the skin comprising passing the article of claim 41 over the skin.

49. A method for cleaning and/or removing make-up from the skin and/or eyes comprising passing the article of claim 41 over the skin and/or eyes.

* * * * *